United States Patent

Long et al.

[11] Patent Number: 5,904,482
[45] Date of Patent: May 18, 1999

[54] TOOTH EXTRACTION DEVICE AND METHOD OF USING THE SAME

[76] Inventors: Lance Leroy Long, 7515 PikeView Ct.; Dorothy Fern Rossi, 895 Field St., both of Lakewood, Colo. 80215

[21] Appl. No.: 09/017,385

[22] Filed: Feb. 3, 1998

[51] Int. Cl.⁶ ............................................. A61C 3/14
[52] U.S. Cl. ............................................... 433/159
[58] Field of Search ................... 433/4, 159; 606/206, 606/157, 205; 81/417, 321, 427, 416; 294/99.2

[56] References Cited

U.S. PATENT DOCUMENTS

| | | | |
|---|---|---|---|
| D. 154,898 | 4/1949 | Balackmon | D17/6 |
| D. 223,121 | 3/1972 | Feuer | D7/5 |
| D. 322,390 | 12/1991 | Nimtz et al. | D8/395 |
| D. 322,749 | 12/1991 | Snite | D8/395 |
| 1,033,942 | 7/1912 | Ruggles . | |
| 1,358,300 | 11/1920 | Dailey | 433/162 |
| 1,707,947 | 4/1929 | Zettervall . | |
| 1,725,173 | 8/1929 | Anderson . | |
| 2,267,836 | 12/1941 | Parkin | 433/162 |
| 2,514,802 | 7/1950 | Schuessler et al. | 81/321 |
| 2,595,683 | 5/1952 | Lo Monte . | |
| 2,645,013 | 7/1953 | Mathison | 433/159 |
| 3,126,005 | 3/1964 | Smialowski | 606/158 |
| 3,191,304 | 6/1965 | Mattern | 433/159 |
| 3,507,043 | 4/1970 | Rubin | 433/4 |
| 4,001,940 | 1/1977 | Cusato . | |
| 4,023,450 | 5/1977 | Ygfors | 81/418 |
| 4,310,305 | 1/1982 | Frajdenrajch | 433/4 |
| 4,727,876 | 3/1988 | Porat et al. | 433/159 |
| B1 4,217,686 | 8/1980 | Dragan | 29/413 |

*Primary Examiner*—John J. Wilson
*Attorney, Agent, or Firm*—Fields and Johnson, P.C.

[57] ABSTRACT

The tooth extraction device includes a pair of handle members with opposing jaws and a force limiting spring or biasing member interconnecting the handle members to provide an adjustable and selective force to be applied to a targeted tooth. A pin is mounted between the handle members and may be positioned so that more or less clamping force is exerted upon the tooth. The jaws of the handle members have contacting surfaces which surround a concave or recessed area, and the jaws have a curved shape enabling the jaws to effectively grasp teeth of different sizes and at different locations in the mouth. The method of the invention includes the steps of preselecting a desired amount of clamping force to be applied to the targeted tooth by choosing a first set point, engaging the tooth with the extraction device and, if desired, adjusting the amount of force applied to the tooth by selecting a different set point reflective of a different amount of clamping force.

20 Claims, 4 Drawing Sheets

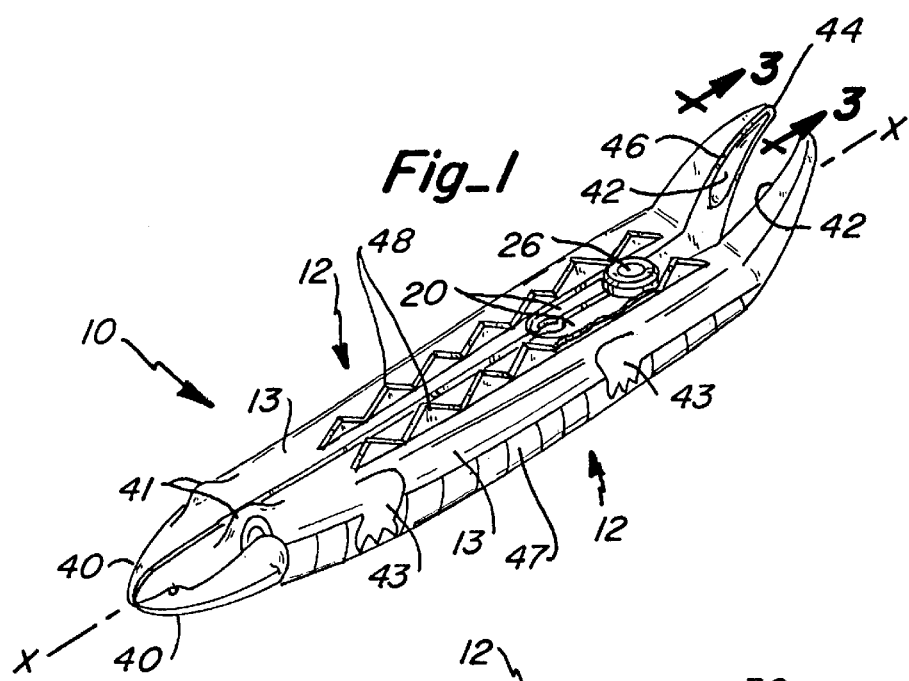
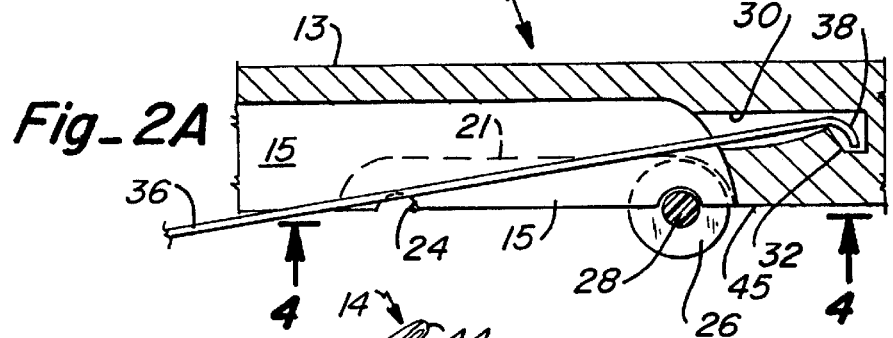
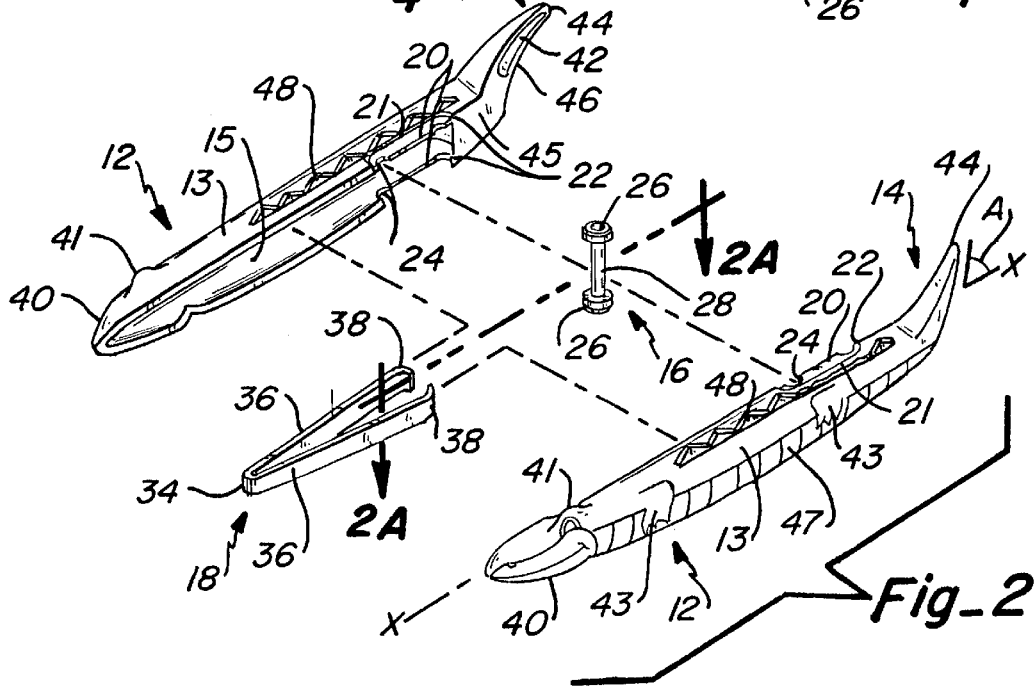

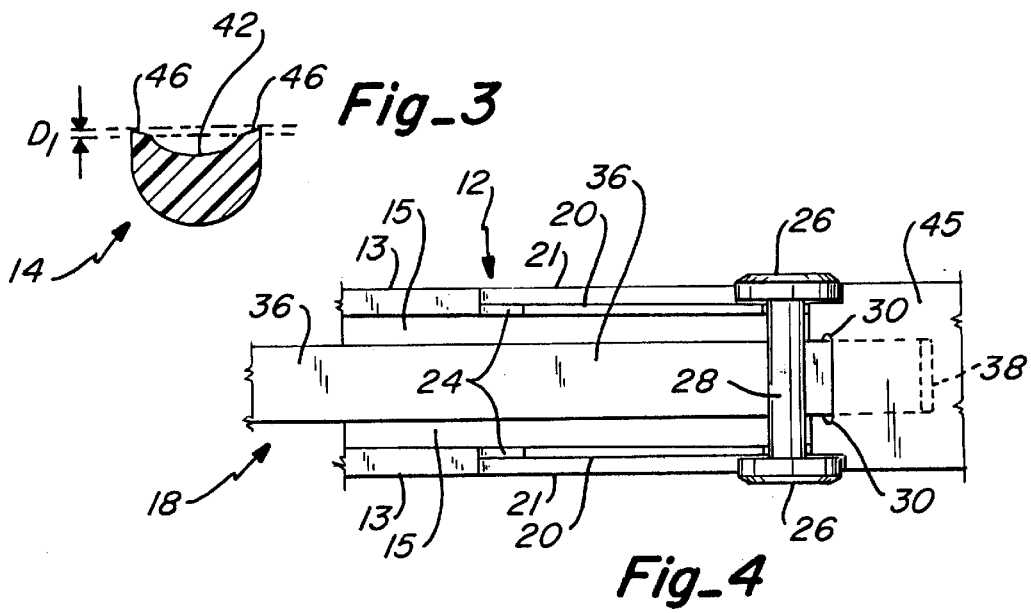
Fig_3
Fig_4
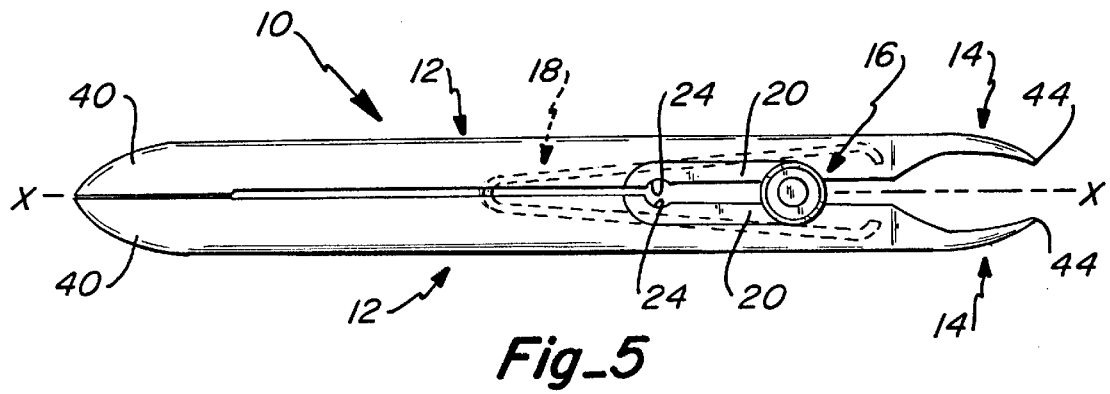
Fig_5
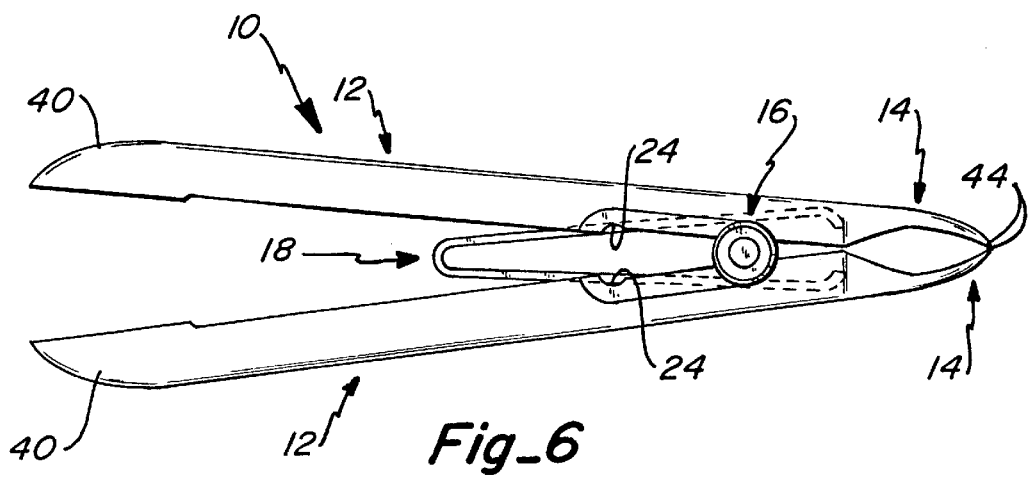
Fig_6

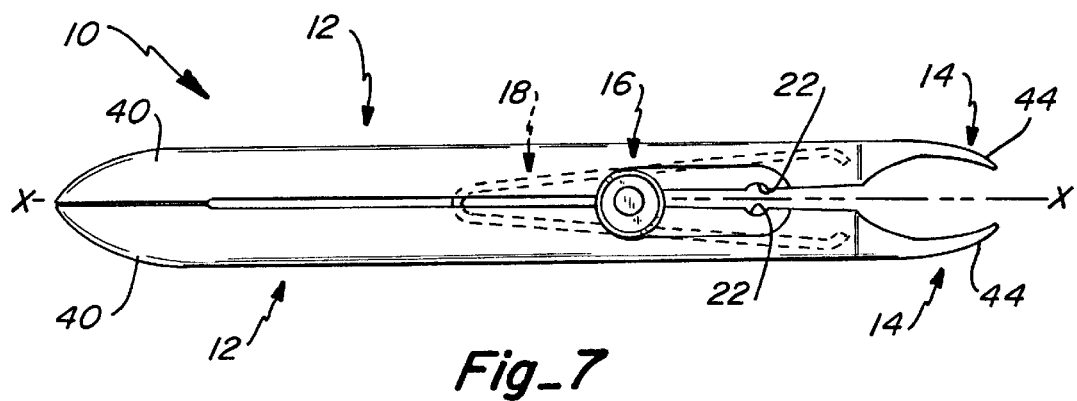
Fig_7
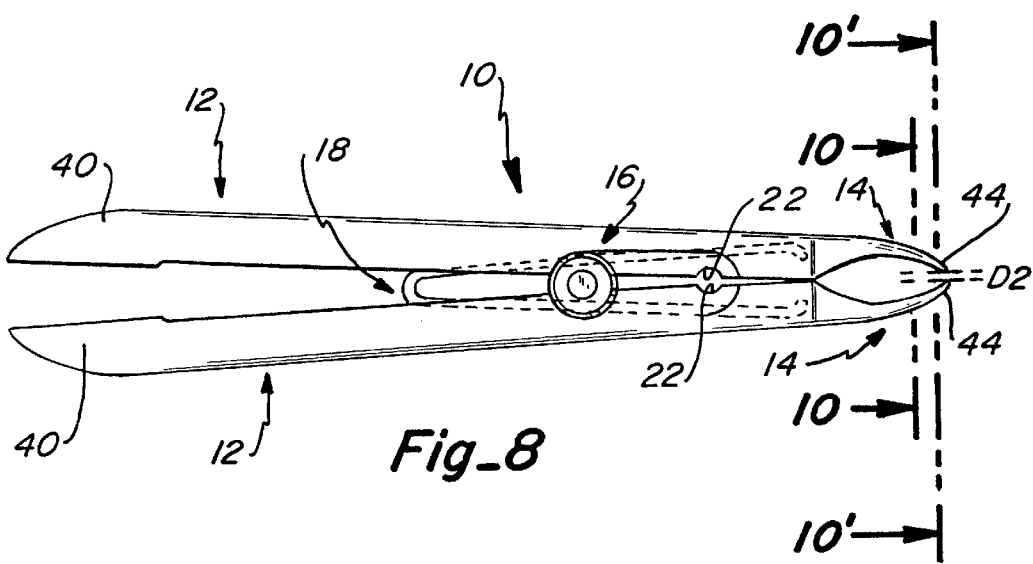
Fig_8

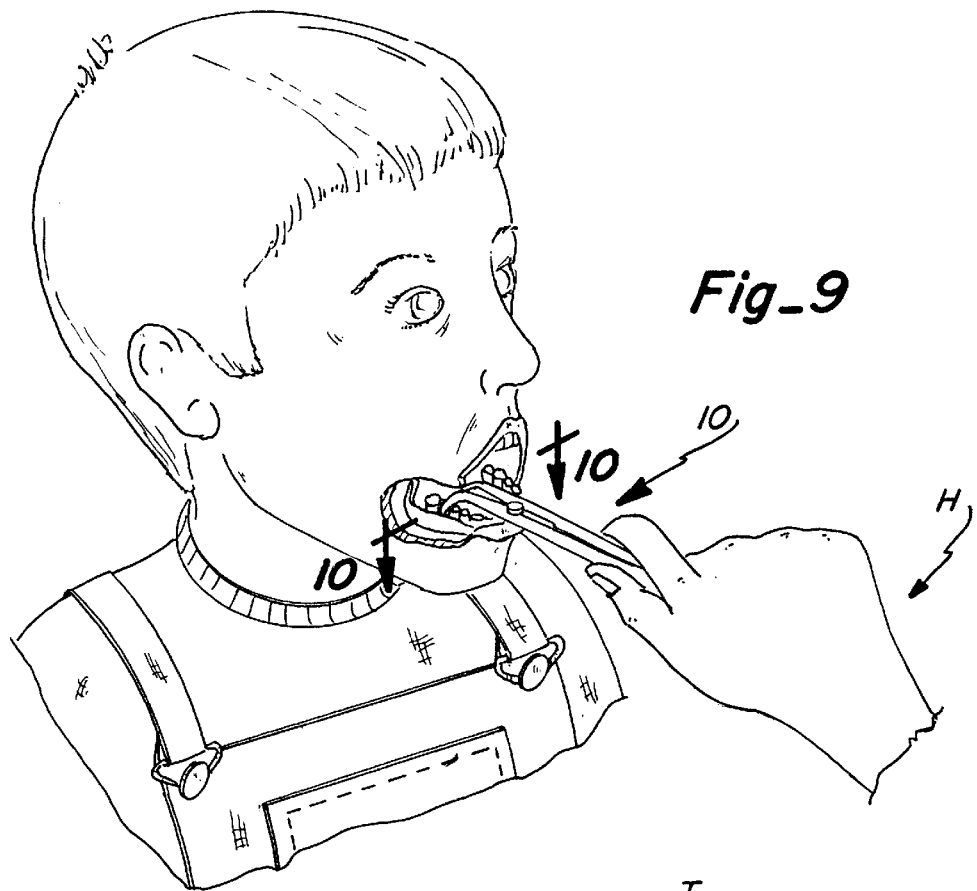
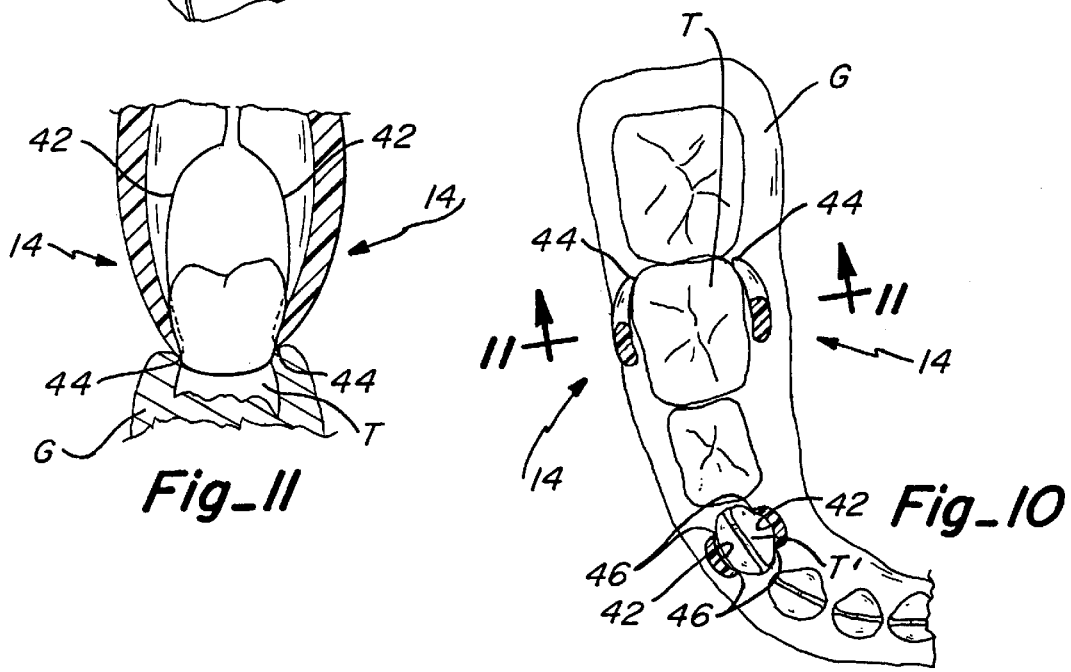

TOOTH EXTRACTION DEVICE AND METHOD OF USING THE SAME

TECHNICAL FIELD

This invention relates to a device for extraction of a tooth and a method of using the device, and more particularly, to a tooth extraction device and method which incorporates a resilient member which can be adjusted to provide a desired amount of clamping force on the tooth to be extracted.

BACKGROUND ART

A number of prior art devices exist for the purpose of extracting a tooth or otherwise holding or clamping teeth during dental and orthodontic procedures. For instruments such as dental forceps, the amount of force applied to a particular tooth is determined by the force which the dentist exerts on the forceps. For dental or orthodontic clamps, the amount of force exerted on a particular tooth is determined by the force of the spring or resilient member used in conjunction with the clamp.

One representative example of medical forceps includes U.S. Pat. No. 4,727,876 to Porat, et al. which discloses plastic gripping members mounted to a pair of handles. The proximal ends of the handles are connected to one another resulting in a biasing force which keeps the forceps in a normally open position.

U.S. Pat. No. 4,001,940 to Cusato discloses an elastic positioner apparatus for orthodontic procedures. This apparatus is also characterized by a pair of handle members connected at their proximal ends resulting in a biasing force which keeps the handle members in a normally open position. The apparatus further includes a cam block which enables the jaws of the handle members to be maintained at a set distance from one another. In an alternative embodiment, Cusato discloses a spring carried by a pin member which urges the jaw tips to a closed position.

U.S. Pat. No. 2,267,836 to Parkin; U.S. Pat. No. 2,645,013 to Mathison; and U.S. Pat. No. 3,191,304 to Mattern are each representative of dental clamps or retainers which are characterized by a pair of opposed handles which are forced to a normally closed position by a spring.

U.S. Pat. No. 3,507,043 to Rubin; U.S. Pat. No. 4,217,686 to Dragan; and U.S. Pat. No. 4,310,305 to Frajdenrajch are representative of orthodontic pliers which also incorporate a spring or biasing member to place the pliers in a normally closed position.

While the foregoing inventions are suitable for their intended purposes, none of them are especially adapted for the removal or extraction of a tooth wherein a preselected and adjustable amount of force may be placed on the tooth by the device in order to remove the tooth.

SUMMARY OF THE INVENTION

For many years, unorthodox and sometimes unsafe methods have been used to extract children's teeth. For example, tying a string around the tooth and then connecting the free end of the string to a door can be both an unsafe and traumatic experience for the child. Use of common household tools are not designed for the tight spaces and odd angles encountered in removing a child's tooth. Additionally, these household tools are not designed to protect delicate adjacent teeth. Dental tools are not readily available to the public because of their expense and distribution channels. Even if such tools were available to the general public, they can be used improperly resulting in injury. One advantage of the invention described herein is one which is especially adapted for tooth removal in a safe manner.

Furthermore, the invention herein is directed to a device which is of a simple and reliable construction for use on all different types of teeth.

Ultimately, there is a need for a simple yet reliable extraction device which may be used in the home to extract the primary teeth of children in a safe and comfortable manner, as well as providing a device with sufficient clamping force to extract the targeted tooth when it is ready to be extracted.

The present invention in its simplest form includes a pair of handle members with opposing jaws and a force limiting spring or biasing member interconnecting the handle members to provide an adjustable and selective force that is applied to the targeted tooth. The handle members may be molded in the shape of an animal to provide an aesthetically pleasing shape to the child. The jaws are angled away from a common axis in which the handle members lie in order that the jaws may more easily grasp teeth which are encountered at different locations within the mouth. The jaws of the handle members are similar in shape and arrangement as the jaws of forceps used by a dentist. The jaws have contacting surfaces which surround a concave or recessed area, and the jaws have a curved shape enabling the jaws to effectively grasp teeth of different sizes at different locations in the mouth. An adjuster member or pin is mounted between the handle members and may be positioned so that more or less clamping force is exerted upon the tooth to be extracted.

Further structure is described in the description of the preferred embodiment which follows. Additional advantages of this invention will become apparent from the following description, taken in conjunction with the accompanying drawings.

BRIEF DESCRIPTION OF THE DRAWINGS

FIG. 1 is a perspective view of the tooth extraction device of this invention;

FIG. 2 is an exploded perspective view of the extraction device illustrating its primary component parts;

FIG. 2A is an enlarged fragmentary horizontal section, taken along line 2A—2A of FIG. 2, illustrating some of the interior structural details of the extraction device when assembled;

FIG. 3 is an enlarged vertical section, taken along line 3—3 of FIG. 1, illustrating the cross-sectional shape of one of the jaws;

FIG. 4 is an enlarged vertical section, taken along line 4—4 of FIG. 2A, further illustrating some of the interior structural elements when assembled;

FIG. 5 is a plan view illustrating the extraction device when placed in a first clamping position resulting in a lessor force which can be exerted upon a tooth, and further illustrating the jaws in a fully open position;

FIG. 6 is another plan view, illustrating the device in the first clamping position and with the jaws placed in a normally closed position;

FIG. 7 is a plan view illustrating the extraction device placed in a second clamping position resulting in a greater force which can be placed upon a tooth, and further showing the jaws in a fully open position;

FIG. 8 is another plan view illustrating the extraction device in the second clamping position with the jaws placed in a normally closed position and wherein a small gap exists between the tips of the jaws;

FIG. 9 is a perspective view of the extraction device of this invention as it is used to extract a tooth from a child;

FIG. 10 is a greatly enlarged fragmentary plan view of the jaw of the child and further illustrating the extraction device being placed on teeth T and T' with horizontal sections taken, respectively, along lines 10—10 and 10'—10' of FIG. 8; and FIG. 11 a vertical section, taken along line 11—11 of FIG. 10, illustrating the extraction device engaging the tooth of the child.

BEST MODE FOR CARRYING OUT THE INVENTION

As shown in FIGS. 1 and 2, a preferred embodiment of the invention is disclosed which illustrates a tooth extraction device 10 characterized by four major members, namely, a pair of handle members 12 which are connected to one another by a spring or resilient member 18, and an adjuster member or pin 16 that is adjustable to vary the force at which a desired tooth is engaged. The handle members 12 may be formed in the shape of an animal such as an allegator or crocodile, as shown. The handle members 12 are further defined as having an outer surface 13 and an inner surface 15 which houses the pin 16 and spring 18, as further discussed below. Jaws 14 are formed at the distal ends of the handle members 12 and offset a desired angle A from longitudinal axis X—X as shown in FIG. 2. Accordingly, the handle members lie substantially along longitudinal axis X—X with the jaws 14 extending away from the axis. The jaws also have a curved shape resulting in the tips of the jaws extending toward one another when the device is assembled.

Each handle member 12 includes pin engaging flanges 20 which are formed adjacent the jaws 14. As best seen in FIGS. 2 and 4, the pin engaging flanges 20 are simply a narrowed or thinned portion of the handle members. The flanges 20 commence at interface line 21 and extend to the edge of the corresponding handle member. A distal indent 22 and a proximal indent 24 may be formed at opposite ends of the pin engaging flanges 20. Additionally, the flanges 20 are formed on both the upper and lower outer surface 13 of the handle members 12. The pin engaging flanges 20 can also be described as slots formed on the upper and lower outer surface of the handle members. The terms "upper" and "lower" are defined as the extraction device is positioned in FIG. 2.

As further shown in FIG. 2, pin 16 includes a pin body 28 and a pair of pin heads 26 formed at opposite ends of the pin body 28. As shown in FIG. 4, pin 16 is positioned between the handle members 12 and the pin heads 26 engage opposing upper and lower slots 20. Pin heads 26 slide along slots 20 and are placed in either a first or second set position within indents 22 and 24 as further discussed below.

Spring 18 is characterized by a spring apex 34 and a pair of spring extensions 36 which each terminate in a curved or hooked portion 38.

Each handle member 12 further includes a head portion 40 and raised portions 41 which correspond to the head and eyes of the animal. The tail of the animal may also define the jaw tips 44. A plurality of animal legs 43 may be provided as protrusions along the handle members, or the legs 43 may simply be printed or stenciled on the outer surface 13. The bottom surface of the handle members may have a ribbed configuration 47 which resembles the under belly of the animal. The upper surface of the handle members may include a plurality of spines or protrusions 48 which resemble the spines or irregular back surface of the animal.

In addition to the raised surface portions 41, spines 48 and under belly 47 having aesthetic value, they also have a utilitarian function in providing additional surface area and a textured surface for enhanced gripping by the user.

Although the shape of the handle members 12 are disclosed as being of an allegator or crocodile shape, it is understood that this shape can be modified in the shape of other animals to provide not only a different aesthetic shape, but also additional surface area/texturing so that the user's hands do not inadvertently slip while holding the handle members.

The inner surface of the jaws 14 as best seen in FIGS. 2 and 3, each include an engaging surface 46 which circumscribes or surrounds a corresponding concave area 42. The engaging surface 46 may be slightly angled so that there is some definable distance between the exterior and interior edges of the engaging surface 46 as illustrated by distance $D_1$ in FIG. 3. The distal end of the handle members 12 near the jaws 14 each include an inner wall 45 which is contiguous with the adjacent engaging surface 46. The inner wall 45 extends proximally to the distal indent 22.

When the extraction device 10 is assembled, each curved end 38 of spring 18 is inserted through an opening or chamber 30 which is formed adjacent the inner wall 45 of each handle member. Opening or chamber 30 may include an enlarged portion 32 adapted to receive a corresponding curved end 38. Prior to engaging the last curved end 38 in an opening 30, pin 16 is positioned so that pin heads 26 align with opposing slots 20. As best seen in FIG. 4, pin heads 26 may slide along the flanges 20 and can be placed either in distal or proximal indents 22 and 44. The pin 16 is prevented from sliding out of the device by the pin heads 26 whose diameter is large enough to span the gap between adjacent edges of opposing slots 20. Furthermore, indents 22 and 24 provide natural stops in order to constrain the pin from freely sliding between the two set positions.

The operation of the device will now be described with reference to FIGS. 5–8. Beginning first with FIG. 5, the pin 16 is shown in a first position in which the pin 16 is placed within the distal indents 22 and the pin body 28 does not come into contact with the adjacent spring extensions 36. Accordingly, the force exerted upon the jaws 14 is solely determined by the resilient force of the spring 18. This first position results in a comparatively lesser amount of force exerted on a tooth as compared to the second position discussed below. FIG. 5 also illustrates the jaws 14 in a fully open position in which the proximal ends of the handle members 12 have been squeezed together and have overcome the biasing force of the spring 18. FIG. 6 also illustrates the pin 16 in the first position, but further shows the jaws 14 in a closed position, after the proximal ends of the handle members 12 have been released.

FIGS. 7 and 8 illustrate the extraction device when the pin 16 has been placed in the second position which allows a greater amount of force to be exerted on the tooth. As shown, pin 16 has been moved to the left and pin body 28 resides in proximal indents 24. As best seen in FIG. 2A, spring extensions 36 are positioned so they intersect with proximal indents 24. Accordingly, the moment arm or effective length of the spring extensions 36 are reduced so that rotation occurs about the pin 16 at the location of proximal indents 24. This reduced moment arm results in a greater force which must be imparted on the handle members to spread the jaws 14 and accordingly results in a greater clamping force exerted by the jaws 14 on a tooth when the handle members are released. FIG. 7 illustrates the device when the jaw are in the finally open position and FIG. 8 illustrates the fully closed position. A small gap shown as distance $D_2$ remains between the jaws 14 when the pin is in the fully closed second position because the spring extensions 36 are forced to a more normal spread position by the pin 16 residing in indents 24.

As is evident from FIGS. 5–8, the handle members 12 function in a reverse manner as compared to standard medical or dental forceps. The force of the spring 18 determines the degree of clamping force applied to a tooth, and not the gripping force of a user. Therefore, a user cannot inadvertently apply too much force to the device which could result in the premature extraction of a tooth or injury to the child.

FIG. 9 illustrates the extraction device 10 held in the hand H of a user who is grasping a lower tooth of a child. The extraction device 10 is inserted in the mouth and the tips 44 of the jaws 14 are pointed downward to engage the base of the lower tooth. Depending upon the amount of force which the user wishes to impart upon the tooth, the pin 16 can be placed in either the first or second position.

FIG. 10 illustrates the engagement of the jaws 14 on both a lower molar tooth T, and a lower anterior tooth T'. Because of the curved and tapered shape of the jaws 14 and the concave area 42 which is surrounded by the engaging surface 46, the jaws 14 may effectively engage a wider molar tooth T, or a smaller and more curved anterior tooth T'. The cross-sectional views of the jaws 14 in FIG. 10 are taken at different sectional lines to illustrate how the jaws are especially adapted to handle teeth of varying sizes and shapes.

FIG. 11 is a vertical section showing the engagement of the molar tooth T wherein the tips 44 of the jaws 14 are placed near the gums G. The concave areas 42 and the engagement surfaces 46 make contact with the tooth enabling the tooth to be securely engaged for removal. Thus, increased surface area is provided to engage the tooth by provision of concave areas 42 and engagement surfaces 46. This increased surface area reduces the possibility of breaking or otherwise fracturing the tooth when it is removed.

The method of this invention is best described with reference to FIGS. 9–11. First, the user determines the amount of force desired to be placed on the tooth to be extracted. If it is desired to have a greater force applied to the tooth, then the pin is placed in the second position of FIGS. 7 and 8. If a lighter force is desired, the pin is placed in the first position of FIGS. 5 and 6. Once the position is determined, the jaws are placed around the targeted tooth and the distal tips 44 of the jaws 14 are placed adjacent the gum line G. Once the jaws 14 have been securely positioned around the targeted tooth, the user simply pulls on the handle members 12 without squeezing them together. In other words, the force of the jaws alone is used to clamp the targeted tooth, and the user grasps the handles in order to displace the tooth from the mouth. If the device is first placed in the first position and the tooth is not successfully extracted, then the device may be placed in the second position and another attempt made in extracting the tooth. Alternatively, if the second position is first chosen and results in undue discomfort experienced by the child because of the degree of clamping force, the device may then be placed in the first position.

The jaws of the device will slip off the tooth if the root of the tooth has not dissolved to the point in which the tooth is ready for extraction. In practice, it has been found that a safe amount of clamping force that can be transferred to the tooth when the device is placed in the second position is a stress on the order of 600 pounds per square inch. This force has been shown to be an adequate amount to allow a tooth to be extracted at the point in time when the tooth is ready for extraction. This stress is based upon a bending moment of 3 pound-inches, a sectional moment of inertia of 0.001 $inches^4$, and a distance from the sectional centroid of the engaging portion of the jaws to the edge of the engaging portion of the jaws of approximately 0.02 inches. The bending moment of 3 pound-inches is based upon a 6-inch moment arm and a 5-pound load which represents the grip strength of the spring. The clamping force produced by the device in the first position may be any desired amount less than that of the second position. Although a value has been provided for the clamping force of the device, it will be understood that a greater or lesser force can be adopted depending upon the intended use of the invention.

Although the preferred embodiment illustrates only two set points, it is within the spirit and scope of this invention to provide additional set points by extending the length of slot 20 and locating the spring 18 so that its effective moment arm can be either reduced or increased by placement of the pin in another indent formed in the slot 20.

The handle members 12 may be constructed of a material such as type 6 nylon, which has sufficient strength to withstand the stresses placed upon a tooth and is easily machinable. The spring 18 may be constructed of a stainless steel material which will not corrode or otherwise oxidize when exposed to moisture. The pin 16 may also be constructed of a material such as nylon. In lieu of type 6 nylon, the handle members may be made from any number of differing types of plastics with sufficient strength to withstand the forces encountered during use.

This invention has been described in detail with reference to a particular embodiment thereof, but it will be understood that various other modifications can be effected within the spirit and scope of the claimed invention.

We claim:

1. A tooth extraction device for removing a desired tooth, said device comprising:

a pair of handle members each including a jaw, said jaws positioned in opposed relation for grasping the tooth, said handle members being substantially aligned with a common axis, and said jaws being offset from said axis a desired angle enabling said jaws to more easily grasp the tooth;

a resilient member connecting said handle members and to provide a selectively adjustable force for grasping the tooth by said jaws; and each said jaw having a corresponding engaging surface, and a concave area delimited by said engaging surface, said engaging surfaces being positioned in opposed relation to grasp substantially opposite sides of the tooth.

2. A device, as claimed in claim 1, further including:

an adjuster located between said handle members and selectively located between said handle members to vary the force of said resilient member.

3. A device, as claimed in claim 2, further including:

a flange formed on each said handle member, and at least two indents communicating with said flange;

said adjuster further including at least one head portion which slidably engages with said flanges, said adjuster being selectively positionable in said indents to define a predetermined amount of force said resilient member provides said jaws.

4. A device, as claimed in claim 1, wherein:
said resilient member includes an apex and a pair of depending extensions, one of said pair of extensions connecting to one of said pair of handle members, and the other of said pair of extensions connecting to the other of said pair of handle members.

5. A device, as claimed in claim 1, wherein:
said jaws are tapered at a distal end thereof.

6. A tooth extraction device for the removal of a desired tooth, said device comprising:
a pair of handle members each including a jaw, said jaws positioned in opposed relation for grasping a tooth, said handle members being substantially aligned with a common axis, and said jaws being offset from said axis at an angle enabling said jaws to more easily grasp the tooth;
a resilient member connecting said handle members and to provide a selectively adjustable force for grasping the tooth by said jaws; and
an adjuster located between said handle members and selectively positionable between said handle members to vary the force of said resilient member.

7. A device, as claimed in claim 6, wherein:
each said jaw includes a corresponding engaging surface and a concave area delimited by said engaging surface, said engaging surfaces being positioned in opposed relation to grasp substantially opposite sides of the tooth.

8. A device, as claimed in claim 6, wherein:
said resilient member includes an apex and a pair of depending extensions, one of said pair of extensions connecting to one of said handle members and the other of said pair of extensions connecting to the other of said handle members.

9. A device, as claimed in claim 6, wherein:
said jaws are tapered at a distal end thereof.

10. A device, as claimed in claim 6, further including:
a flange formed on each said handle member, and at least two indents communicating with said flange;
said adjuster further including at least one head portion which slidably engages with said flanges, said adjuster being selectively positionable in said indents to define a predetermined amount of force said resilient member provides said jaws.

11. A tooth extraction device for the removal of a desired tooth, said device comprising:
means for holding a tooth including a pair of opposing jaws, said holding means being substantially aligned with a common axis, and said jaws being offset from said axis at an angle enabling said jaws to more easily grasp the tooth;
means for creating a resilient force, said creating means connecting said holding means and to provide a selectively adjustable force for grasping the tooth by said jaws; and
means for adjusting the resilient force of said creating means, said adjusting means located between said holding means and selectively positionable therebetween to vary the resilient force of said creating means.

12. A device, as claimed in claim 11, wherein:
each said jaw includes a corresponding engaging surface and a concave area delimited by said engaging surface, said engaging surfaces being positioned in opposed relation to grasp substantially opposite sides of the tooth.

13. A tooth extraction device for the removal of a desired tooth, said device comprising:
means for holding the tooth including a pair of jaws positioned in opposed relation for grasping the tooth, said holding means being substantially aligned with a common axis, and said pair of jaws being offset from said axis at an angle enabling said pair of jaws to more easily grasp the tooth;
means for creating a resilient force connecting said holding means and to provide a selectively adjustable force for grasping the tooth by said pair of jaws; and
each said jaw having a corresponding engaging surface and a concave area delimited by said engaging surface, said engaging surfaces being positioned in opposed relation to grasp substantially opposite sides of the tooth.

14. A device, as claimed in claim 13, further including:
means for adjusting the resilient force of said creating means, said adjusting means located between said holding means and selectively positionable therebetween to vary the resilient force of said creating means.

15. A method of extracting a tooth comprising the steps of:
providing an extraction device including a pair of opposed jaws;
determining an amount of desired force to place on the tooth by contacting the tooth with the jaws;
positioning an adjuster on the device at a first set point according to the desired force;
engaging the tooth to be extracted with the jaws; and
extracting the tooth by pulling on the extraction device.

16. A method, as claimed in claim 15, further including the step of:
repositioning the adjuster to a second set point reflective of another desired force; and
re-engaging the tooth to be extracted.

17. A tooth extraction device for the removal of a desired tooth, said device comprising:
means for holding a tooth, said holding means being resiliently biased to hold the tooth and further including a pair of opposing jaws, each jaw of said pair of jaws having an engaging surface and a concave area delimited by said engaging surface, said concave area extending below said engaging surfaces when viewing said jaws along a vertical cross section, said jaws being offset from said means for holding at an angle enabling said jaws to more easily grasp the tooth; and
means for adjusting the resilient force of said means for holding, said adjusting means positioned between said means for holding to selectively vary the resilient force.

18. A tooth extraction device for removing a desired tooth, said device comprising:
a pair of handle members each having a length, proximal and distal ends, and a jaw formed on each said distal ends thereof;
means for resiliently connecting said handle members;
an adjuster located between said handle members to vary the force of said means for resiliently connecting;
each of said jaws being offset from their corresponding handle member at an angle enabling said jaws to more easily grasp the tooth; and
each said jaw including an engaging surface and a concave area delimited by said engaging surface, said jaws being positioned in opposed relation to grasp substantially opposite sides of the tooth.

19. A tooth extraction device for removing a desired tooth, said device comprising:

a pair of handle members each having a length, proximal and distal ends, and a jaw formed on each said distal ends thereof;

means for resiliently connecting said handle members;

each of said jaws being offset from their corresponding handle member at an angle enabling said jaws to more easily grasp the tooth;

each said jaw including an engaging surface and a concave area delimited by said engaging surface, said jaws being positioned in opposed relation to grasp substantially opposite sides of the tooth; and said means for resiliently connecting includes an apex and a pair of depending extensions, one extension of said pair of extensions connecting to one handle member of said pair of handle members, and the other extension of said pair of extensions connecting to the other handle member of said pair of handle members.

20. A tooth extraction device for removing a desired tooth, said device comprising:

a pair of handle members each having a length, proximal and distal ends, and a jaw formed on each said distal ends thereof;

means for resiliently connecting said handle members;

each of said jaws being offset from their corresponding handle member at an angle enabling said jaws to more easily grasp the tooth;

each said jaw including an engaging surface and a concave area delimited by said engaging surface, said jaws being positioned in opposed relation to grasp substantially opposite sides of the tooth;

an adjuster located between said handle members to vary the force of said means for resiliently connecting;

a flange formed on each said handle member between said proximal and distal ends thereof, and at least two indents communicating with said flange; and said adjuster further including at least one head portion which slidably engages with said flanges, said adjuster being selectively positionable in said indents to define a predetermined amount of force provided by said means for resiliently connecting.

* * * * *